(12) United States Patent
Zeller et al.

(10) Patent No.: US 9,417,172 B2
(45) Date of Patent: Aug. 16, 2016

(54) LABORATORY REACTOR WITH A REACTION VESSEL

(71) Applicant: IKA—Werke GmbH & Co. KG, Staufen (DE)

(72) Inventors: Andreas Zeller, Bad Krozingen (DE); Erhard Eble, Bad Krozingen (DE)

(73) Assignee: IKA—Werke GmbH & Co. KG, Staufen (DE)

( * ) Notice: Subject to any disclaimer, the term of this patent is extended or adjusted under 35 U.S.C. 154(b) by 8 days.

(21) Appl. No.: 14/315,695

(22) Filed: Jun. 26, 2014

(65) Prior Publication Data

US 2014/0308180 A1    Oct. 16, 2014

Related U.S. Application Data

(63) Continuation-in-part of application No. 13/000,833, filed as application No. PCT/EP2009/003383 on May 13, 2009, now abandoned.

(30) Foreign Application Priority Data

Jun. 24, 2008 (DE) .......................... 10 2008 029 900

(51) Int. Cl.
*B01J 19/18* (2006.01)
*G01N 5/00* (2006.01)
*B01J 19/00* (2006.01)
*B01F 15/00* (2006.01)
*B01L 7/00* (2006.01)
*B01F 7/16* (2006.01)

(52) U.S. Cl.
CPC ............ *G01N 5/00* (2013.01); *B01F 15/00194* (2013.01); *B01F 15/00311* (2013.01); *B01J 19/00* (2013.01); *B01F 7/16* (2013.01); *B01L 7/00* (2013.01); *B01L 2300/02* (2013.01); *B01L 2300/14* (2013.01)

(58) Field of Classification Search
CPC ..................... B01J 19/18; B01J 2219/00209
USPC ................................................. 422/135, 259
See application file for complete search history.

(56) References Cited

U.S. PATENT DOCUMENTS 5,284,627 A    2/1994 Brazelton et al.

*Primary Examiner* — Natalia Levkovich
(74) *Attorney, Agent, or Firm* — Volpe and Koenig, P.C.

(57) ABSTRACT

A laboratory reactor (1) with a reaction vessel (2) for receiving media or substances to be processed has devices or units for processing or mixing media or components and for measuring, the devices or units being able to engage in the reaction vessel or reactor vessel (2) from above or below. On the lower side of the base (5), the laboratory reactor (1) has placement feet (6) which are mounted movably or flexibly and are connected to a weight measuring device or to sensors belonging to a weight-measuring device such that the weight of the product to be processed or a change in weight can be determined without complicated additional weighing operations.

10 Claims, 2 Drawing Sheets

LABORATORY REACTOR WITH A REACTION VESSEL

INCORPORATION BY REFERENCE

The following documents are incorporated herein by reference as if fully set forth: U.S. patent application Ser. No. 13/000,833, filed Jan. 10, 2011; International Application No. PCT/EP2009/003383, filed May 13, 2009; and German Patent Application No. DE 102008029900.6, filed Jun. 24, 2008.

BACKGROUND

The invention relates to a laboratory reactor with a reaction vessel, closed and connected to a device for changing the pressure, i.e. with a device for creating overpressure or a vacuum, to accept media to be processed and/or to be mixed and/or to be made reacting with each other or at least with one processing and/or measuring aggregate or mixing and/or agitating device engaging said vessel, as well as a holder for receiving said vessel, which has a base facing a support area.

Such laboratory reactors are known in multiple forms and different designs. Frequently they are designed in a modular fashion and serve to optimize and reproduce chemical reaction, mixing, dispersing, and/or homogenization processes on a laboratory scale. For example, the following processes can be performed thereby:

- the production of cremes, lotions, emulsions, and liposome-preparations of the pharmaceutical and cosmetic field,
- the integration of solid matters, such as calcium carbonate, talcum, titanium dioxide, and other substances into liquid polymers,
- the integration of additives and solid polymer compounds into mineral oils,
- the grinding and defibration of solid matter and fibers in liquids and polymers.

Such laboratory reactions can frequently be adjusted by the user to the respective objective. Here, for example temperature measuring devices, agitators, dispersing devices, and/or thermostats can be used, and also be adjusted in various manners, such as program-controlled via computers and/or microprocessors. Here, single-walled and dual-walled vessel can be used with or without bottom drains made from a special glass or stainless steel, with generally the basic equipment includes a stand system for connecting on the one hand the vessel and on the other hand the arrangements, apparatuses, and measuring devices to be used. The connection for the devices is frequently embodied such that the processing and measuring devices can be mounted above the vessel so that they can engage the vessel from above.

Additionally, laboratory reactors are known in which a drive shaft for a mixing device is inserted into the vessel through the bottom.

In such laboratory reactors for the processing of substances, frequently importance is given to very precisely (defined) amount, which during the processing may change, if applicable, and which are to be filled either successively or also simultaneously, or which may change during processing with regards to their weight or due to chemical reactions, if for example a heating function is included.

In order to allow filling or refilling or gradually adding additional material during processing it had to be ensured in the past that such substances are added in precisely the correct amount, i.e. each of them had to be measured in advance. This is considered cumbersome and expensive.

SUMMARY

Therefore the object is to provide a laboratory reactor of the type defined at the outset, by which the filling, refilling, and/or adding can be performed in a simple and controlled fashion.

In order to attain this object the laboratory reactor defined at the outset is characterized such that on the bottom of the holder several placement feet are provided or connected or effectively fastened, in their operating position pointing upwards or in a vertical direction, supported in an elastic or adjustable or movable fashion against a return or spring force.

In this way it is possible, during the processing of substances, to determine changes of the amount to be processed, for example by way of evaporation, and to introduce substances or products, subsequently to be added, in their correct weight or amount without being required to separately dose the components to be added. Additionally, if necessary a constant monitoring of the weight of the processed mixture of substances is possible. Further, a very precise dosing of individual components of the mixture can occur during their filling process into an already installed reaction vessel.

It is particularly beneficial for a part of the movable support of the placement foot or feet to be effectively connected to a weighing device. Here, a simple design option is to render the mobility of the placement feet to be effective at a weighing or measuring device.

In a modified embodiment the placement foot or feet may comprise at least partially a spring-elastic material and include a transmission element to the weighing device based on the elasticity of the placement foot or placement feet.

It is particularly beneficial if several or, preferably, all placement feet are supported in an elastic or movable fashion and provided on or connected to a weighing device. This results in a particularly precise weighing of mixtures and components of mixtures.

Another modified version may provide that at least two placement feet or several or all placement feet are connected to each other mechanically. This is another way to impinge or control an appropriate weighing device.

The connection of two placement feet may show a distance between them and the support area or at least two support feet can be connected in one piece to form a wide support foot, which comprises or impinges a joint weighing device or two separate ones. In this way, the stability of the laboratory reactor can be improved and simultaneously the weighing function can be achieved. With regards to common laboratory reactors having several individual placement feet an embodiment is preferred, though, in which these several individual placement feet each cooperate with one weighing device, for example via appropriate sensors, such that even existing laboratory reactors can largely remain unchanged, but may be retrofitted with the respective movable and elastic placement feet comprising a weighing function.

A preferred embodiment may provide that the elastic or adjustable or movable placement feet impinge levers or rockers or end pieces, which cooperate with the weighing device or are in an effective connection therewith or alternatively comprise a weighing device.

The levers or rockers or end pieces, movable via the placement feet, may be provided with sensors for measuring force or with measuring strips or Piezo-elements as the components of a weighing device. This way, an appropriate weighing function can be realized within a minimum amount of space.

It is beneficial for the sensors for measuring forces of several or all placement feet to be combined with a microprocessor or a computer such that the weight forces compensated at the individual placement feet are added and/or averaged. This way, right from the start the user is provided with one weight statement and/or a total weight or its change can be displayed in a suitable fashion or be forwarded to a control device, which can react to the change of weight.

One embodiment of the laboratory reactor according to the invention may provide that it comprises an electronic storage for recipes, in which individual components of mixtures are stored, defined according to substance and weight, and thus the integrated weighing function can be processed menu controlled. This way, frequently repeated processing and mixing steps can be considerably automated and streamlined.

Another embodiment may provide that an operating, control, and/or storage unit is arranged at and connected to the laboratory reactor or a housing in a detachable fashion and is connected to the driving parts, located in the laboratory reactor or the housing, to the weighing device and/or additional aggregates by way of a radio or cable connection. This way, the user can also operate the laboratory reactor from a greater distance and/or read the various displays, which is advantageous for example when the laboratory reactor shall be operated under a protective cover, for example an exhaust, and the user still intends to perform operation functions.

The agitation and/or mixing device or processing aggregate of the laboratory reactor may provide a torque detection, which may particularly occur via the current draw of the drive motor. If applicable, if a speed control is provided, its setting may also be used to determine the torque. If the torque changes due to a change in viscosity, this may also be a reason to add one or more substances, with here it may be important that this occurs by a predetermined weight, which is easily possible in a simple fashion using the placement feet and the weighing device.

The device to change the pressure, i.e. to create an overpressure or preferably a vacuum in the reaction vessel, sealed appropriately tightly, may also be a pump, for example a vacuum pump, connected or able to be connected to the laboratory reactor or the reactor vessel. Thus, this device for changing the pressure may be allocated to the laboratory reactor regardless if said device is a direct part of the laboratory reactor or an independent, separate device. This may lead to a change of weights in another processing step of materials or substances in the laboratory reactor, which can be detected by the weighing device according to the invention and corrected, if necessary.

Primarily in combinations of individual or several of the above-described features and measures a laboratory reactor develops, in which the weight of the matter to be processed or made to react and any potential change in weight, either during processing or during the addition of other components, can immediately be recognized and detected and, if necessary, corrected or evaluated.

BRIEF DESCRIPTION OF THE DRAWINGS

In the following an exemplary embodiment of the invention is explained in greater detail using the drawing. It shows, in a partially schematic illustration.

DETAILED DESCRIPTION OF THE PREFERRED EMBODIMENTS

Figure 1:
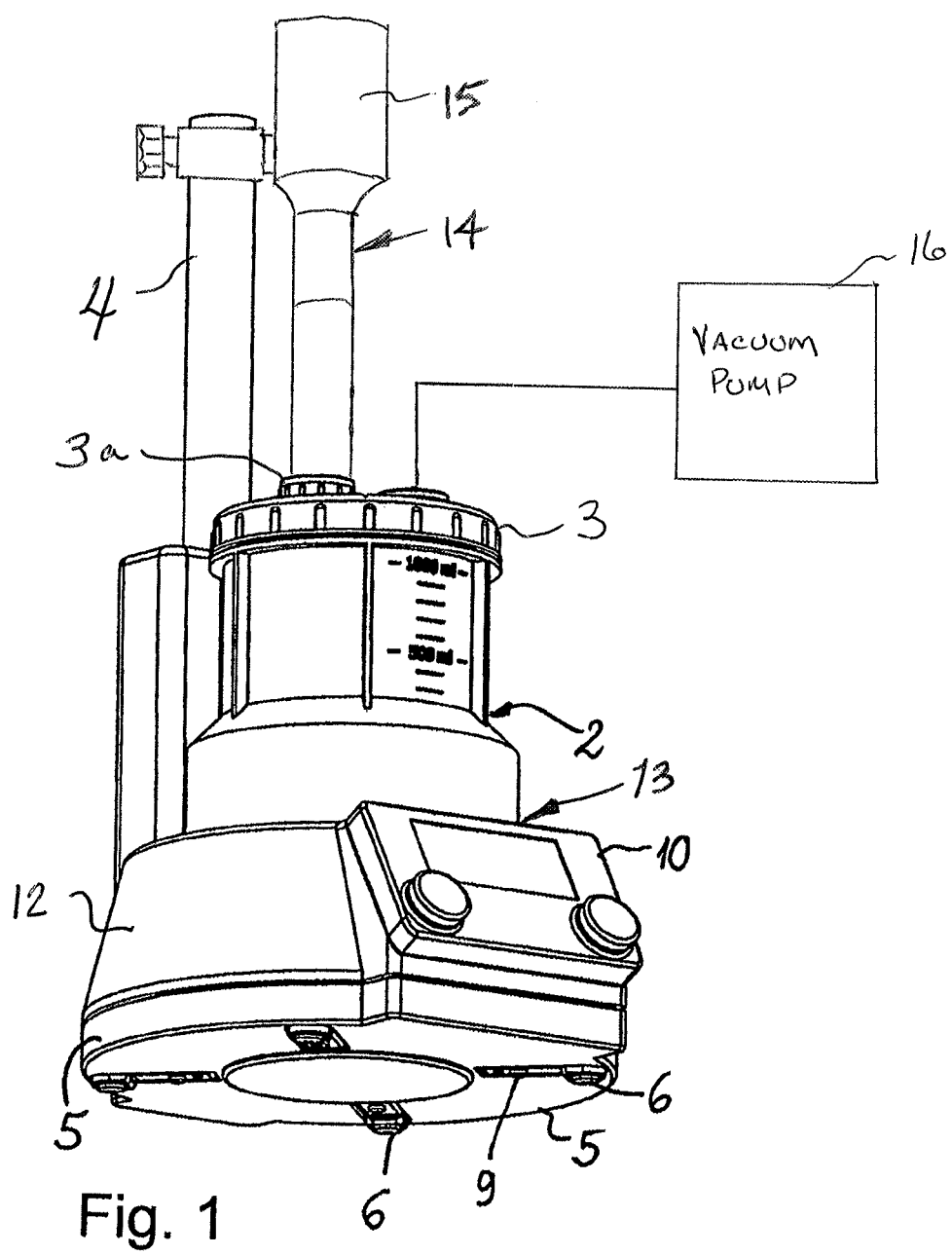
FIG. 1 is a perspective view of a laboratory reactor according to the invention with a reaction vessel and a fastening rod for mounting processing and/or measuring aggregates or devices, such as mixers and/or agitators, dispersing or homogenization devices, with a fastening to the ground being provided, at which placement feet are arranged at the bottom.

In the exemplary embodiment a laboratory reactor, marked 1 in its entirety, comprises a reactor or reaction vessel, marked 2 in its entirety, for accepting and processing substances, which shall be processed and/or mixed in a suitable manner or can react with each other, which in turn can occur via processing and/or measuring devices and aggregates, such as a disperser 14 having a motor 15, which are known to those of ordinary skill in the art, for example the T10 basic available from Ika-Werke, Staufen, Germany, and which may be inserted into the reaction vessel 2, for example, in the area 3a of the lid 3. Alternatively, at or in the area of the lid 3 a device, for changing the pressure in the appropriately sealed reaction vessel 2 may be connected or potentially connected, for example a pump or a vacuum pump 16 which are known to those of ordinary skill in the art, such as the SC-920 from Ika-Werke, Staufen, Germany. Such devices may be fastened at a fastening rod 4, allocated to the overall fastener of the laboratory reactor 1, for example in an adjustable and/or detachable fashion, if such aggregates or devices are not engaging the reaction vessel or reactor vessel 2 from below. The reaction vessel 2 is received in a holder 13 on the housing 12 of the laboratory reactor 1.

Figure 2:
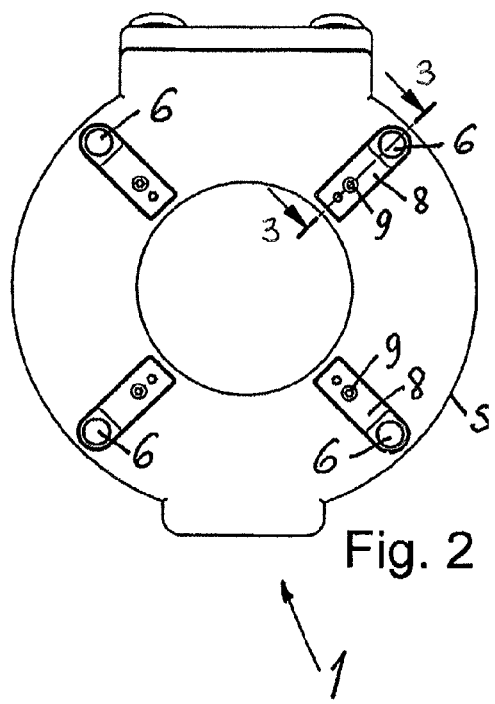
FIG. 2 is a view of the bottom of the base of the laboratory reactor.

In the exemplary embodiment according to FIG. 2 the laboratory reactor 1 as a whole can be placed upon a support area and for this purpose it comprises four placement feet 6 at the bottom of its base 5, shown particularly in FIG. 2, facing said support area. In the operating position according to FIGS. 3 and 4, they are supported in an elastic or adjustable or movable fashion upwards or in the vertical direction against a return force or spring force, indicated by arrows in FIG. 4, and are provided or connected or in an effective connection to a weighing device 18 in a manner to be described in the following such that the weight of the reactor or reaction vessel 2 and its content can be determined and monitored. Additionally the material to be processed can be correctly dosed with regards to weight and one or more components can also be added subsequently with their weight portions being correct, with any changes in weight occurring in this context immediately being detected and monitored by the weighing device.

The placement feet 6 are here supported on the base 5 of the laboratory reactor 1, with its bottom facing the support area.

Figure 4:
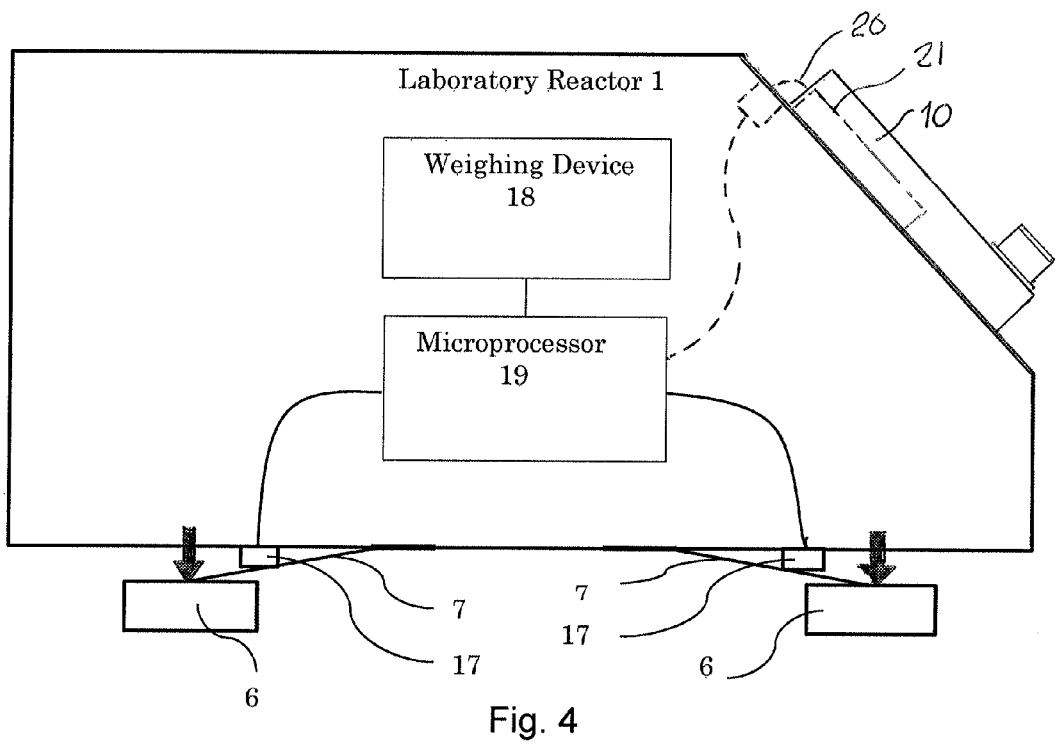
FIG. 4 is a schematic diagram of one arrangement of the laboratory reactor of FIG. 1.
Figure 3:
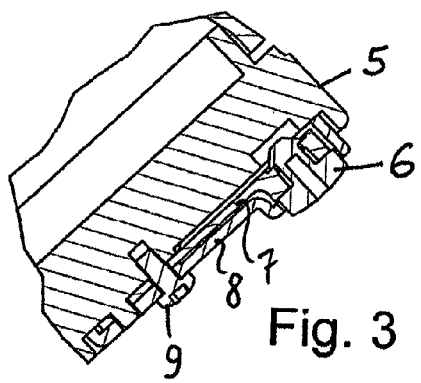
FIG. 3 is an enlarged longitudinal cross-section through the base in the area of an placement foot according to the sectional line 3-3 in FIG. 2.

According to FIGS. 3 and 4, it is provided that a portion of the movable support of the placement feet 6 is in an effective connection to the weighing device 18, either directly or through a computer or microprocessor 19. Here, it is discernible that the placement feet 6 each impinge or are supported on a lever 7 made of a spring-elastic material, preferably embodied as a spring, which is deflected by an increase of the weight force and thus a stronger displacement of the foot 6 into its support. These spring-like levers 7, movable by the placement feet 6, may be provided or cooperate with force-measuring sensors or measuring strips or Piezo-elements, indicated as 17 in FIG. 4, which form part of a weighing device. This way, with increasing weight the motion of the foot 6 may deform the elastic lever 7 into the base 5 to a greater extent and transfer said deformation via the above-mentioned sensors to the weighing device 18.

Here, the lever 7 embodied as a spring is protected at its bottom by a cover 8, shown in FIG. 3, and thus it cannot be activated unintentionally. This cover 8 and the elastic lever 7 are here fastened and/or stretched by a screw 9 to the base 5, a shown in FIG. 3.

The force measuring sensors 17 of all placement feet 6 can here be combined, in a manner not shown in greater detail, with the microprocessor or computer 19, shown in FIG. 4, so that all weight force—portions compensated by the individual placement feet 6 can be added to a total weight.

In FIG. 1, an operating unit 10 is discernible on the laboratory reactor 1, which may also be embodied as a control and/or storage unit, such as a memory indicated at 21 in dot-dash lines, and be detachably connected to the laboratory reactor 1 or a housing allocated thereto, and connected via radio frequency or a cable connection, for example as indicated in broken lines at 20 to drive parts or aggregates located in the laboratory reactor 1 or its housing. In this way, the operating unit 10 can also be operated at a distance from the actual laboratory reactor 1, if the laboratory reactor 1 shall be used at a position hard to access.

The agitator(s) and/or mixer(s) or processing aggregate(s), either engaging the reactor vessel 2 from above through a lid 3 or from below, may comprise torque detection, not shown in greater detail, which may particularly occur via the power draw of the drive engine of such a device or aggregate. Further, a speed control may be provided at an agitator and/or mixer or processing aggregate, with its setting may serve to determine the torque.

In FIG. 1 it is discernible that the reactor or reaction vessel 2 is closed and this allows for the provision of a device for changing the pressure, i.e. a device for creating an overpressure or a vacuum such as the vacuum pump 16, in order to allow influencing the reaction of the substance located inside the vessel 2.

The laboratory reactor 1 with a reaction vessel 2 for accepting media or substances to be processed comprises devices or aggregates to process or mix media or components or also to measure them, which can engage the reaction or reactor vessel 2 from above or also from below. At the bottom of the base 5 the laboratory reactor 1 comprises placement feet 6, which are supported in a movable or elastic fashion and which are connected to a weight measuring device 18, preferably via sensors 17 allocated to a weight measuring device 18 such that the weight of the substance to be processed or any change of weight can be determined without any expensive additional weighing processes.

The invention claimed is:

1. A laboratory reactor (1) comprising:
   a closed reaction vessel (2) having a closure, the closed reaction vessel is adapted to accept substances to be processed or to be mixed or to be made reacting with each other,
   a device for changing pressure connected to the closed reaction vessel,
   an agitating device (14) engaging said vessel (2),
   a holder (13) for receiving the vessel (2), which has a base (5) facing a support area,
   several placement feet (6) located at a bottom of the holder, supported for movement in an upward direction against a return force,
   sensors (17) that are arranged to cooperate with the placement feet (6), and
   a weighing device and a processor, wherein the sensors are connected to the weighing device via the processor, which is configured to determine a total weight based on sensor inputs from the sensors.

2. The laboratory reactor according to claim 1, wherein the placement feet (6) directly contact the sensors (17).

3. The laboratory reactor according to claim 1, wherein at least one of the placement feet (6) is supported via a spring-elastic material and is provided with a transfer element that contacts the sensors connected to the weighing device.

4. A laboratory reactor according to claim 1, wherein all of the placement feet (6) are supported in a movable fashion and connected to the sensors.

5. A laboratory reactor according to claim 1, wherein at least two of the placement feet (6) are mechanically connected to each other.

6. A laboratory reactor according to claim 1, further comprising levers (7), wherein the placement feet (6) impinge the levers (7) which cooperate with the sensors.

7. A laboratory reactor according to claim 6, wherein the sensors comprise force measurement sensors, and the levers (7), movable by the placement feet (6) cooperate with the force measurement sensors.

8. A laboratory reactor according to claim 7, wherein the force measurement sensors are located at least at several of the placement feet (6) and outputs thereof are combined by the processor in a manner such that weight forces compensated by the individual placement feet are added.

9. A laboratory reactor according to claim 1, further comprising:
   a non-transitory storage medium having an electronic storage for recipes, in which individual components or components of mixtures for the recipes are defined according to a material and weight are stored and are processable utilizing integrated weighing functions.

10. A laboratory reactor according to claim 1, wherein the device for changing the pressure, to create an overpressure or a vacuum in the laboratory vessel (2) upon it being sealed, is a pump (16) is connectable to the laboratory reactor (1).

* * * * *